United States Patent [19]

Khan et al.

[11] Patent Number: 5,512,199
[45] Date of Patent: * Apr. 30, 1996

[54] HAND WIPE SOLUTION

[75] Inventors: Mohammed A. Khan, Sandy; Minh Q. Hoang, Taylorsville, both of Utah

[73] Assignee: Becton Dickinson and Company, Franklin Lakes, N.J.

[*] Notice: The portion of the term of this patent subsequent to Jun. 15, 1999, has been disclaimed.

[21] Appl. No.: 147,181

[22] Filed: Nov. 2, 1993

[51] Int. Cl.$^6$ ..................................................... C11D 3/48
[52] U.S. Cl. ................................................................ 252/106
[58] Field of Search .................................................. 252/106

[56] References Cited

U.S. PATENT DOCUMENTS

| | | | |
|---|---|---|---|
| 4,202,881 | 5/1980 | Gross et al. | 424/70 |
| 4,957,908 | 9/1990 | Nelson | 514/55 |
| 5,164,107 | 11/1992 | Khan et al. | 252/106 |
| 5,180,061 | 1/1993 | Khan et al. | 206/570 |
| 5,298,242 | 3/1994 | Vanlerberghe et al. | 424/78.36 |
| 5,334,388 | 8/1994 | Hoang | 252/106 |

FOREIGN PATENT DOCUMENTS

72440/87  5/1986  Australia ............... A47L 13/17

Primary Examiner—José G. Dees
Assistant Examiner—Joseph M. Conrad, III
Attorney, Agent, or Firm—Nanette S. Thomas; Bruce S. Weintraub

[57] ABSTRACT

An antimicrobial wipe composition for use as a hand washing agent, comprising an alcohol, an active antimicrobial agent, a water soluble polymer, a polyalkylene glycol, an emollient and water. The hand wipe composition does not require scrubbing, prepping, washing and rinsing, will not irritate the skin and will provide antimicrobial effectiveness to the skin.

10 Claims, No Drawings

HAND WIPE SOLUTION

BACKGROUND OF THE INVENTION

1. Field of the Invention

This invention relates to an antimicrobial wipe composition for use as a hand washing agent that will not irritate or dry the skin. The antimicrobial wipe composition does not require scrubbing, prepping, washing and rinsing.

2. Description of Related Art

Healthcare professionals attending to patient care wash their hands to control the spread of infection in the hospital environment from patient to patient. However, it is believed that the hand washing procedure is not practiced to the extent that it should be. However, surgical procedures are routinely proceeded by surgical hand scrubbing and patient pre-operative prepping. The use of antimicrobial agents is common in surgical scrubs and patient pre-operative prepping solutions. But when it comes to patient care, professionals often do not have time to attend to hand washing from patient to the next. This slack in the patient care procedure could cause the spread of infectious diseases not only to other patients but to the healthcare professionals themselves.

Hand washing procedures are performed in several ways. Several procedures include an ordinary antimicrobial bar soap, a surgical scrub or preoperative prepping agent or rubbing alcohol. The use of these procedures repeatedly is hard and rough on hands.

Therefore, it is desirable to produce a hand washing agent which is easy to use, mild and gentle to the hands and packaged for easy access.

SUMMARY OF THE INVENTION

The present invention is a hand wiping formulation that requires no scrubbing, washing and rinsing and provides antimicrobial effectiveness. The hand wiping formulation desirably comprises an alcohol, an active antimicrobial agent, a water soluble polymer, a polyalkylene glycol, a moisturizer and/or emollient and water.

Most preferably, the hand wiping formulation composition comprises:

(a) from about 50% to about 80% of an alcohol;

(b) from about 0.01% to about 2.0% of an active antimicrobial agent;

(c) from about 0.01% to about 2.0% of a water soluble polymer;

(d) from about 0.5% to about 5.0% of a polyalkylene glycol;

(e) from about 0.5% to about 5.0% of a moisturizer and/or emollient; and (f) from about 6% to about 50% of water.

A significant advantage of the hand wipe formulation of the present invention is its use in the healthcare profession as an effective means for washing hands without scrubbing and rinsing while providing substantial antimicrobial effectiveness, as well as non-irritancy or drying to the skin.

A further advantage of the hand wipe formulation of the present invention is its ease of use not requiting lengthy time to decontaminate the hand as compared to conventional scrub techniques.

DETAILED DESCRIPTION

The present invention may be embodied in other specific forms and is not limited to any specific embodiments described in detail which are merely exemplary. Various other modifications will be apparent to and readily made by those skilled in the art without departing from the scope and spirit of the invention. The scope of the invention will be measured by the appended claims and their equivalents.

The hand wipe formulation is most preferably the following composition:

(a) an alcohol;

(b) an active antimicrobial agent;

(c) a chitosan or a high polymer amine;

(d) a polyalkylene glycol;

(e) a moisturizer and/or emollient; and (f) water.

An alcohol is preferably used in the antimicrobial formulation because of its bactericidal properties. Generally, a concentration of alcohol over 50% is an effective germicidal agent. It kills gram-positive, gram-negative bacteria fungi; and many viruses. This potent activity of alcohol against micro-organisms is due to its denaturation of proteins and enzymes and dehydration.

An alcohol for use in the antimicrobial formulation includes, but is not limited to, ethyl alcohol and isopropyl alcohol.

The preferred alcohol for use in the antimicrobial formulation is isopropyl alcohol. Preferably, isopropyl alcohol may be present in the antimicrobial formulation in an amount from about 50 to about 80 weight percent, and most preferably at about 60 weight percent.

Since degerming of the skin completely is impossible, because microbial flora will grow up after a period of time, a small amount of a suitable antimicrobial agent is included in the formulation. An antimicrobial agent is a compound or substance that kills microorganisms or prevents or inhibits their growth and reproduction.

The antimicrobial agent present in the antimicrobial formulation composition is selected so as not to upset desirable physical and chemical properties of human skin. A properly selected antimicrobial agent maintains stability under use and storage conditions (pH, temperature, light, etc.), for a required length of time. A desirable property of the antimicrobial agent is that it is safe and nontoxic in handling, formulation and use, is environmentally acceptable and cost effective.

Classes of antimicrobial agents include, but are not limited to, chlorophenols, biguanides, antibiotics and biologically active salts.

The preferable antimicrobial agent in the antimicrobial is bronopol, chlorhexidine diacetate, TRICOSAN™, hexetidine or parachlorometaxylenol (PCMX). Preferably, chlorhexidine diacetate or hexetidine is present in the antimicrobial formulation in an amount from about 0.0 1 to about 2.0 weight percent and most preferably at about 0.5 weight percent.

To counter the drying of skin by alcohol, an emollient and/or humectant is included in the formulation, such as a water soluble polymer. A chitosan is a high polymer amine and adapted to form salts with acids and is typically characterized as a water soluble polymer.

A preferred chitosan in the antimicrobial composition is a chitosonium pyrrolidone carboxylate, Kytamer® PC (trademark of Amerchol Corporation, Edison, N.J.) sold by Amerchol.

A chitosan is used in the antimicrobial formulation for leaving a film on the skin after wiping whereby the antimicrobial agent is released from the film as needed. The selection of the chitosan is also based on its film forming, biocompatible and humectant properties due to the basic amino acid present in the chitosan. Chitosan contains a skin moisturizing factor and binds with the skin.

Preferably, chitosan is present in the antimicrobial formulation in an amount from about 0.01 to about 2.0 weight percent, and most preferably at about 0.05 weight percent.

A polyalkylene glycol is used in the antimicrobial formulation for lubricating and conditioning of the skin and also as a compliment to the skin soothing action of the chitosan. A polyalkylene glycol is a synthetic oily substance and is typically characterized as a skin conditioner. The selection of a polyalkylene glycol is based on its biocompatibility and its ability to protect the skin from drying and chapping.

A preferable polyalkylene glycol in the antimicrobial composition is a 14 butyl ether, UCON® Fluid AP emollient (trademark of Amerchol Corporation, Edison, N.J.) sold be Amerchol.

Preferably, the polyalkylene glycol is present in the antimicrobial composition in an amount from about 0.5 to about 5.0 weight percent and most preferably at about 1.0 weight percent.

Emollients in their physical form are thin liquids, oils of various viscosities, fatty solids or waxes. Hydrocarbons function essentially as emollients by virtue of their ability to lubricate and/or hold water at the skin surface due to their relative occlusivity. Mineral oil is such a fluid. Some emollients are hydrophilic (glycerin, propylene glycol) and are water soluble lubricants and humectants. Since emollients may be fatty chemicals, oily or waxy in nature, they can impart barrier properties to formulations and are then referred to as moisturizers.

Moisturizers are substances which provide external lubricant behavior, such as to soften and soothe the skin because they encourage skin water retention.

The function of the moisturizer and/or emollient in the antimicrobial formulation is to provide relief for dry and sensitive skin. Therefore, chapping of the skin may be prevented. In addition, the moisturizer and/or emollient does not leave a tacky after feel on the skin.

Suitable moisturizers and/or emollients in the antimicrobial formulation includes lanolin, derivatives of lanolin such as the ethoxylated acetylated alcohol and surface active alcohol derivatives of lanolin, propylene glycol, polypropylene glycol, polyethylene glycol, lanolin and lanolin derivatives, mineral oils, fatty alcohols and glycerin.

A preferable moisturizer and/or emollient for the antimicrobial formulation is a polyethyl glycol lanolin derivative, PEG® 75 lanolin (trademark of Amerchol Corporation, Edison, N.J.) sold by Amerchol Corporation. Lanolin is a good emollient and works well as a wetting agent needed to wet the skin.

Another preferable moisturizer and/or emollient for the antimicrobial formulation is an ethoxylated (75 moles) lanolin, Solulan® L-575 (trademark of Amerchol Corporation, Edison, N.J.) sold by Amerchol Corporation.

Preferably, a moisturizer and/or emollient is present in the antimicrobial formulation in an amount from about 0.5 to about 5.0 weight percent and most preferably at about 1.0 weight percent.

It is preferred that the hand wipe formulation be prepared and adapted for liquid application in solution or emulsion form, and most conveniently, in spray application form (i.e., aerosol spray type containers).

The hand wiping composition of the present invention is prepared by first mixing the alcohol and water. Then the chitosan is completely solubilized in the alcohol and water mixtures. The remaining ingredients are then added and mixed until a clear homogeneous liquid solution is obtained. The liquid composition can be filled into a bottle, a spray can or pump dispenser. Most preferably, the composition is dispensed out of a bottle.

Other ingredients which are conventional or desirable in various cosmetic formulations may also be added to the hand wiping formulation as long as they do not adversely affect the overall properties of the antimicrobial agent in the formulation.

If desired, the hand wiping formulation of the invention may include a perfume to provide a pleasing scent or a dye to provide a characteristic color.

The following examples are not limited to any specific embodiment of the invention, but are only exemplary.

EXAMPLE 1

PREPARATION OF HAND WIPING FORMULATION

The hand wipe formulation of the present invention was prepared with the following ingredients:

TABLE I

| Ingredients | Weight Percent | | | | |
| --- | --- | --- | --- | --- | --- |
| | A | B | C | D | E |
| Isopropyl Alcohol | 60.00 | 60.00 | 60.00 | 60.00 | 60.00 |
| Water | 37.44 | 37.44 | 37.44 | 37.44 | 37.44 |
| PEG ®-75 Lanolin | 1.00 | 1.00 | 1.00 | 1.00 | 1.00 |
| UCON ® Fluid Oil | 1.00 | 1.00 | 1.00 | 1.00 | 1.00 |
| Kytamer ® PC | 0.05 | 0.05 | 0.05 | 0.05 | 0.05 |
| Antimicrobial agent: | — | — | — | — | — |
| Bronopol | 0.5 | — | — | — | — |
| Chlorhexidine Diacetate | — | 0.5 | — | — | — |
| Triclosan ™ | — | — | 0.5 | — | — |
| Parachlorometaxylenol | — | — | — | 0.5 | — |
| Hexetidine | — | — | — | — | 0.5 |
| Fragrance | 0.01 | 0.01 | 0.01 | 0.01 | 0.01 |

In a mixing vessel, isopropyl alcohol and water were first mixed together. Then the Kytamer® was mixed in with the alcohol and water until the Kytamer® was completely solubilized. PEG® 75 lanolin, U-Con® fluid oil, the antimicrobial agent and fragrance were then continuously mixed into the alcohol, water and Kytamer® mixture to obtain a clear homogenous solution.

EXAMPLE 2

BACTERICIDAL EFFECTIVENESS EVALUATION

The formulations from EXAMPLE 1 were evaluated for bactericidal characteristics against target micro-organisms, namely *Staphylococcus Aureus, Pseudomonas Aeruginosa, Escherichia Coli,* and *Candida Albicans*. These are the standard micro-organisms representing gram positives, gram negatives and fungis classifications. The bactericidal effectiveness testing procedure was conducted as follows:

5 ml of the formulation was added to a sterile tube. A microbial challenge of 0.1 ml containing the target microorganism with appropriate count was added to the 5 ml test solution. At exposure times of 1 and 5 minutes, a 1.0 ml sample was transferred to 9.0 ml of D-E neutralizing broth. Subsequent 1.0 ml samples were transferred to D-E neutralizing broth base. The procedure was performed at full strength and at dilution's of 1:10 and 1:100 or at other appropriate dilutions. All samples were incubated at 30°–35° C. for 48 hours.

The results of the effectiveness testing is given below in the tables that follow. Since the hand wiping solution is intended to be used undiluted, the killing power of the solution at that dilution is the most important factor to be considered. However, testing was conducted at several dilutions to assess the bactericidal power of the solution.

TABLE 2

BACTERICIDAL EFFICACY OF FORMULATION A

| Staphylococcus Aureus Challenge: $2.5 \times 10^6$ CFU | | Pseudomonas Aeruginosa Challenge: $3.4 \times 10^6$ CFU | |
|---|---|---|---|
| Dilution | Kill time (min) | Dilution | Kill time (min) |
| FS | 1 | FS | 1 |
| 1:2 | 1 | 1:2 | 1 |
| 1:4 | Positive | 1:4 | Positive |
| 1:6 | Positive | 1:6 | Positive |
| 1:8 | Positive | 1:8 | Positive |

| Candida Albicans Challenge: $10^4$–$10^5$ CFU | | Escherichia Coli Challenge: $1.9 \times 10^7$ CFU | |
|---|---|---|---|
| Dilution | Kill time (min) | Dilution | Kill time (min) |
| FS | 1 | FS | 1 |
| 1:2 | 1 | 1:2 | 1 |
| 1:4 | 5 | 1:4 | Positive |
| 1:6 | 5 | 1:6 | Positive |
| 1:8 | Positive | 1:8 | Positive |

TABLE 3

BACTERICIDAL EFFICACY OF FORMULATION B

| Staphylococcus Aureus Challenge: $2.8 \times 10^7$ CFU | | Pseudomonas Aeruginosa Challenge: $2.8 \times 10^7$ CFU | |
|---|---|---|---|
| Dilution | Kill time (min) | Dilution | Kill time (min) |
| FS | 1 | FS | 1 |
| 1:10 | 5 | 1:10 | 1 |
| 1:100 | Positive | 1:100 | 1 |

| Candida Albicans Challenge: $3.5 \times 10^5$ CFU | | Escherichia Coli Challenge: $2.7 \times 10^7$ CFU | |
|---|---|---|---|
| Dilution | Kill time (min) | Dilution | Kill time (min) |
| FS | 1 | FS | 1 |
| 1:10 | 1 | 1:10 | 1 |
| 1:100 | 1 | 1:100 | 1 |

TABLE 4

BACTERICIDAL EFFICACY OF FORMULATION C

| Staphylococcus Aureus Challenge: $2.8 \times 10^7$ CFU | | Pseudomonas Aeruginosa Challenge: $2.8 \times 10^7$ CFU | |
|---|---|---|---|
| Dilution | Kill time (min) | Dilution | Kill time (min) |
| FS | 1 | FS | 1 |
| 1:10 | 1 | 1:10 | Positive |
| 1:100 | Positive | 1:100 | Positive |

| Candida Albicans Challenge: $3.5 \times 10^5$ CFU | | Escherichia Coli Challenge: $2.7 \times 10^7$ CFU | |
|---|---|---|---|
| Dilution | Kill time (min) | Dilution | Kill time (min) |
| FS | 1 | FS | 1 |
| 1:10 | Positive | 1:10 | Positive |
| 1:100 | Positive | 1:100 | Positive |

TABLE 5

BACTERICIDAL EFFICACY OF FORMULATION D

| Staphylococcus Aureus Challenge: $2.8 \times 10^7$ CFU | | Pseudomonas Aeruginosa Challenge: $2.8 \times 10^7$ CFU | |
|---|---|---|---|
| Dilution | Kill time (min) | Dilution | Kill time (min) |
| FS | 1 | FS | 1 |
| 1:10 | Positive | 1:10 | Positive |
| 1:100 | Positive | 1:100 | Positive |

| Candida Albicans Challenge: $3.5 - 10^5$ CFU | | Escherichia Coli Challenge: $2.7 \times 10^7$ CFU | |
|---|---|---|---|
| Dilution | Kill time (min) | Dilution | Kill time (min) |
| FS | 1 | FS | 1 |
| 1:10 | Positive | 1:10 | Positive |
| 1:100 | Positive | 1:100 | Positive |

TABLE 6

BACTERICIDAL EFFICACY OF FORMULATION E

| Staphylococcus Aureus Challenge: $2.8 \times 10^7$ CFU | | Pseudomonas Aeruginosa Challenge: $2.8 \times 10^7$ CFU | |
|---|---|---|---|
| Dilution | Kill time (min) | Dilution | Kill time (min) |
| FS | 1 | FS | 1 |
| 1:10 | 1 | 1:10 | 1 |
| 1:100 | Positive | 1:100 | Positive |

| Candida Albicans Challenge: $3.5 \times 10^5$ CFU | | Escherichia Coli Challenge: $2.7 \times 10^7$ CFU | |
|---|---|---|---|
| Dilution | Kill time (min) | Dilution | Kill time (min) |
| FS | 1 | FS | 1 |
| 1:10 | 1 | 1:10 | 1 |
| 1:100 | 1 | 1:100 | 1 |

Note:
FS = Full strength
Positive = Not killed in 5 minutes

As is reported above, all of the formulations will work as hand wipes for disinfection. However, Formulation B, containing chlorhexidine diacetate and Formulation E, containing hexetidine are very effective against all four mircoor-

EXAMPLE 3

Formulations B and E from EXAMPLE 1 were tested for primary skin irritation. Healthy, femal New Zealand white rabbits were obtained from A. C. Daly, Farmville, N.C. The animals were individually housed and identified by an ear tag. The animals' backs were clipped free of fur. Two sites were chosen on each rabbit, with the skin left intact on one site and the skin abraded on the other site. 0.5 ml of each formulation was applied to each test site, covered with gauze, and wrapped with an occlusive binder. After 24 hours, the binder was removed and an evaluation of the skin for erythema and edema was performed. A subsequent evaluation was performed 72 hours post application. The results are reported in Table 7.

TABLE 7

| | | DERMAL REACTION | | | |
|---|---|---|---|---|---|
| | RABBIT | 24 HOURS | | 72 HOURS | |
| TAG NO. | REACTION | ABRAD-ED | IN-TACT | ABRAD-ED | IN-TACT |
| 6778 | ERYTHEMA | 0 | 0 | 0 | 0 |
| | EDEMA | 0 | 0 | 0 | 0 |
| 6779 | ERYTHEMA | 0 | 0 | 0 | 0 |
| | EDEMA | 0 | 0 | 0 | 0 |
| 6780 | ERYTHEMA | 0 | 0 | 0 | 0 |
| | EDEMA | 0 | 0 | 0 | 0 |
| 6775 | ERYTHEMA | 0 | 0 | 0 | 0 |
| | EDEMA | 0 | 0 | 0 | 0 |
| 6776 | ERYTHEMA | 0 | 0 | 0 | 0 |
| | EDEMA | 0 | 0 | 0 | 0 |
| 6777 | ERYTHEMA | 0 | 0 | 0 | 0 |
| | EDEMA | 0 | 0 | 0 | 0 |

EVALUATION OF SKIN REACTION:

| ERYTHEMA AND ESCHAR FORMATION: | VALUE | EDEMA FORMATION: | VALUE |
|---|---|---|---|
| No erythema | 0 | No edema | 0 |
| Very slight erythema (barely perceptible | 1 | Very slight edema (barely perceptible) | 1 |
| Well-defined erythema | 2 | Slight edema (edges of area well defined by definite raising) | 2 |
| Moderate to severe erythema | 3 | Moderate edema (raised approx. 1 mm) | 3 |
| Severe erythema (beet redness to slight eschar formation injuries in depth) | 4 | Severe edema (raised more than 1 mm and extending beyond the area of exposure) | 4 |

DATA ANALYSIS:

| INDEX* | EVALUATION |
|---|---|
| 0.00 | No irritation |
| 0.01–0.99 | Irritation barely perceptible |
| 1.00–1.99 | Slight irritation |

TABLE 7-continued

| DERMAL REACTION | |
|---|---|
| 2.00–2.99 | Mild irritation |
| 3.0–5.99 | Moderate irritation |
| 6.00–8.00 | Severe irritation |

*Total of 48 individual scores = Primary Irritation Index for erythema and edema $$0/24 = \frac{24}{24}$$

What is claimed is:

1. A hand wiping formulations that requires no scrubbing, washing and rinsing comprising:
   (a) an alcohol;
   (b) an antimicrobial agent;
   (c) a water soluble polymer;
   (d) a polyalkylene glycol;
   (e) a moisturizer and/or emollient; and
   (f) water 2. The hand wiping formulation of claim 1 wherein said volatile liquid is isopropyl or ethyl alcohol.

3. The hand wiping formulation of claim 2 wherein said antimicrobial agent is bronopol, chlorhexidine diacetate, TRICLOSAN™ hexetidine or parachlorometaxylenol.

4. The hand wiping formulation of claim 3 where said water soluble polymer is chitosan.

5. The hand wiping formulation of claim 4 wherein said moisturizer and/or emollient is lanolin.

6. A hand wiping formulation comprising:
   (a) an alcohol in an amount from about 50 to about 80 weight percent of the total composition;
   (b) an active antimicrobial agent in an amount from about 0.01 to about 2.0 weight percent of the total composition;
   (c) a water soluble polymer in an mount from about 0.01 to about 2.0 weight percent of the total composition;
   (d) a polyalkylene glycol in an amount from about 0.5 to about 5.0 weight percent of the total composition;
   (e) a moisturizer and/or emollient in an amount from about 0.5 to about 5.0 weight percent of the total composition; and
   (f) water in an amount from about 6 to about 50 weight percent of the total composition.

7. The hand wiping formulation of claim 6 wherein said alcohol is isopropyl or ethyl alcohol.

8. The hand wiping formulation of claim 7 wherein said antimicrobial agent is bronopol, chlorhexidine diacetate, TRICLOSAN™ hexetidine or parachlorometaxylenol.

9. The hand wiping formulation of claim 7 wherein said water soluble polymer is chitosan.

10. The hand wiping formulation of claim 9 wherein said moisturizer and/or emollient is lanolin.

\* \* \* \* \*

UNITED STATES PATENT AND TRADEMARK OFFICE
CERTIFICATE OF CORRECTION

PATENT NO. : 5,512,199
DATED : April 30, 1996
INVENTOR(S) : Mohammed A. Khan, Minh Q. Hoang It is certified that error appears in the above-identified patent and that said Letters Patent is hereby corrected as shown below:

On the title page, item (*), change "Jun. 15, 1999" to -- Sep. 15, 2013 --.

Signed and Sealed this

Twenty-seventh Day of May, 1997

Attest:

BRUCE LEHMAN

*Attesting Officer*  *Commissioner of Patents and Trademarks*